United States Patent [19]

Danielson

[11] Patent Number: 5,170,057
[45] Date of Patent: Dec. 8, 1992

[54] METHOD AND APPARATUS FOR MEASURING THE PARTIAL PRESSURE OF A GAS IN A VACUUM

[75] Inventor: Philip Danielson, Downers Grove, Ill.

[73] Assignee: Danielson Associates, Inc., Lisle, Ill.

[21] Appl. No.: 836,258

[22] Filed: Feb. 18, 1992

[51] Int. Cl.$^5$ .................... G01N 7/04; G01N 21/33
[52] U.S. Cl. ...................................... 250/373; 250/372
[58] Field of Search ............... 250/373, 372, 343, 564

[56] References Cited

U.S. PATENT DOCUMENTS

| | | | |
|---|---|---|---|
| 3,946,235 | 3/1976 | Young | 250/373 |
| 4,652,756 | 3/1987 | Ryan et al. | 250/343 |
| 4,660,297 | 4/1987 | Danielson | 34/4 |
| 4,709,150 | 11/1987 | Burough et al. | 250/343 |

FOREIGN PATENT DOCUMENTS 56-2536  1/1981  Japan .................. 250/343

OTHER PUBLICATIONS

*Fundamentals of Vacuum*, chapter 5 "Vacuum Measurements".

Primary Examiner—Carolyn E. Fields
Attorney, Agent, or Firm—Milton S. Gerstein; Marvin N. Benn

[57] ABSTRACT

Vacuum gauge that detects and measures the partial pressure of a gas in a chamber, from pressures ranging from atmospheric to ultra-high vacuum. The gauge utilizes electromagnetic radiation, that is generated in the vacuum chamber by a electromagnetic radiation source. When the partial pressure of water vapor is being measured, the light source used emits low wavelength UV light in the 184 and 254 nanometer range. For other gases, different light sources emitting different UV wavelengths or different electromagnetic radiation are used. The electromagnetic radiation traverses the interior of the vacuum chamber, and impinges upon a detector. As this light passes through the interior space between the source and the detector, it strikes the particular, residual gas molecules that are being detected. These impacts scatter the light and/or absorb the light, so that there is less photonic energy striking the detector. The greater the number of molecules (the higher pressure) the lower the amount of energy that strikes the detector. Thus, the energy striking the detector is a measure of the partial pressure of the particular gas. In the preferred embodiment, for measuring the partial pressure of water vapor, the gauge-apparatus of the invention utilizes an ultraviolet light source that is surrounded by a hollow cylinder made of nickel, which serves as a detector element via the photoelectric effect.

28 Claims, 3 Drawing Sheets

METHOD AND APPARATUS FOR MEASURING THE PARTIAL PRESSURE OF A GAS IN A VACUUM

BACKGROUND OF THE INVENTION

The present invention is directed to a vacuum gauge for detecting and/or measuring the partial pressure of a gas, such as, for example, water vapor or carbon monoxide.

Present vacuum gauges for measuring the total pressure of gases in a vacuum chamber are numerous. They may be classified into three main groups: Mechanical action gauges induced by pressure differentials; thermal conductivity gauges of the residual gases; and ionization gauges of the residual gases.

Gauges of the first group—mechanical action gauges—use a technique that makes the actual pressure of the residual gases perform work that can be measured. Bourdon tubes or mechanical diaphragm gauges are examples. In most cases, this technique is only usable at vacuum levels that do not extend below rough vacuum. One notable difference to this is the capacitance manometer-gauge, where tiny movements of a thin, metal diaphragm are detected with a capacitance-measuring circuit, and can measure up to high vacuum.

Gauges of the second group—thermal conductivity-gauges, are based on a common technique where the rate of heat loss from a heated wire is proportional to the total pressure. The more molecules present in the vacuum, the greater the heat loss. Examples of these gauges are Pirani and thermocouple gauges, and they are used in various degrees, from atmospheric pressure down to $10^{-3}$ torr, or very slightly below.

Gauges of the third group—ionization gauges—use a technique that is the most common for measuring pressures below $10^{-3}$ torr The technique employs a heated cathode that is used as a source of electrons to ionize the residual gases. The ions are collected and the resultant ion current is measured, which measurement is proportional to the pressure.

While the above-described, prior-art vacuum-gauges work well for measuring the total pressure of a vacuum-chamber, they are not used for measuring the partial pressure of a gas in a vacuum-chamber. The need, or desire, to measure and know the partial pressure of a particular gas within a vacuum-chamber is very important for many vacuum processes, where a relatively large presence of the particular gas could adversely affect the vacuum process. For example, in the well-known vacuum processes of sputtering and plasma etching, which processes are performed usually between $10^{-3}$ and 10 torr total pressure, water vapor is ofttimes inadvertantly introduced or liberated from the vacuum-chamber walls while the processes are being carried out. Since water vapor is highly, and adversely, reactive to these processes, it is extremely important to detect and measure the amounts of water vapor present, in order to prevent the loss of the product.

There are many instruments and techniques currently available for detecting and measuring gases and the partial pressure of a gas, where the total pressure is at, or near, atmospheric. For vacuum environments, however, present technology currently offers a mass spectrometer to measure partial pressures of gases. However, the mass spectrometer can only be used at pressures below $10^{-4}$ torr. For higher pressures, the only techniques and instruments currently available to measure partial gas-pressure are complicated, very expensive, gas-handling and pressure reduction systems.

There are many other vacuum processes where the detection of a gas and the measurement of its partial pressure are extremely important. For example, the presence of carbon monoxide in a vacuum chamber has a negative influence and causes a loss of the level of control in the process of crystal growth, where the presence of CO causes surface defects, haze and pits in the crystals. It is extremely important to detect and measure the presence of CO in the vacuum chamber in order to reduce the quantity to acceptable, quality-control levels.

SUMMARY OF THE INVENTION

It is the primary objective of the present invention to provide a vacuum gauge that detects and measures the partial pressure of a gas.

It is another objective of the present invention to provide such a partial-pressure gauge that operates, not only below $10^{-4}$ torr, as does a mass spectrometer, but also in higher pressure regions up to atmospheric, in which regions a mass spectrometer is not capable of being used.

It is yet another objective of the present invention to provide such a partial-pressure gauge that is relatively inexpensive to produce and maintain, and which can, for all intents and purposes, replace the costly mass spectrometer for pressures below $10^{-4}$ torr, and replace the very complicated and very expensive gas-handling and pressure reduction systems for pressures above $10^{-4}$ torr.

According to the invention, there is provided a gauge-apparatus for measuring the partial of gas in a vacuum environment ranging from atmospheric to $10^{-10}$ torr. The gauge-apparatus utilizes physical phenomena that have never been used in pressure-measurement techniques in vacuum technology. The gauge-apparatus of the invention makes use of ultraviolet (UV) light generated in a vacuum chamber by a light source. When the partial pressure of water vapor is being measured, the light source used emits low wavelength UV light in the 184 and 254 nanometer range. For other gases, different light sources emitting different UV wavelengths or different electromagnetic radiation is used. The light traverses the interior of the vacuum chamber, and impinges upon a detector. As this light passes through the interior space between the source and the detector, it strikes the particular, residual gas molecules that are being detected. These impacts scatter the light and/or absorb the light, so that there is less photonic energy striking the detector. The greater the number of molecules (the higher pressure) the lower the amount of energy that strikes the detector. Thus, the energy striking the detector is a measure of the partial pressure of the particular gas, and, hence, by measuring the energy striking the detector, a measure of the quantity of the particular gas is achieved, thus giving a reading of that gas' partial pressure.

In the preferred embodiment, for measuring the partial pressure of water vapor, the gauge-apparatus of the invention utilizes an ultraviolet light source that is a low pressure, mercury arc lamp with an output spectrum that contains 185 and 254 nanometer wavelength components. The lamp is a commercially available device manufactured by Danielson Associates, Inc., Lisle, Ill., under the name "PHOTOTRON", which is disclosed in U.S. Pat. No. 4,660,297, which patent is hereby incorporated herein. The "PHOTOTRON" is used for desorbing water from the inner walls of a vacuum chamber, which is accomplished since the water molecules absorb photonic energy from the UV light irradiating them. The lamp is surrounded by a hollow cylinder made of nickel, which serves as a detector element. In operation, the UV lamp is turned on, and the UV radiation passes into the vacuum space. A portion of the UV radiation impinges upon the nickel cylinder and causes it to eject photoelectrons via the photoelectric effect. The number of molecules in the residual gases between the UV lamp source and the nickel cylinder vary widely with pressure. Impacts between the photons from the UV radiation cause scattering and energy loss, so that the nickel is bombarded with more photons at higher energy at low pressures than at high pressures. The total photoelectron ejection from the nickel is proportional to the number and energy of the photons striking it. The nickel cylinder is electrically connected to a lead that passes through an insulated feed through the walls of the vacuum system, into an electrometer, and to ground. The electrometer measures the current flow caused by the ejection of the photoelectrons. This current, then, is used as a measure of the partial pressure of the water vapor. For measuring the partial pressure of different gases, the electromagnetic radiation may be different, and/or the wavelength may be different. For example, for the measurement of the partial pressure of carbon monoxide (CO) gas, an ultraviolet radiation light source that emits UV radiation in the 335 nm. range is used instead. For other gases, infrared radiation is used. The particular electromagnetic radiation used, as well as its wavelength, will depend upon the particular gas being measured.

BRIEF DESCRIPTION OF THE DRAWING

The invention will be more readily understood with reference to the accompanying drawing, wherein.

DETAILED DESCRIPTION OF THE INVENTION

Figure 1:
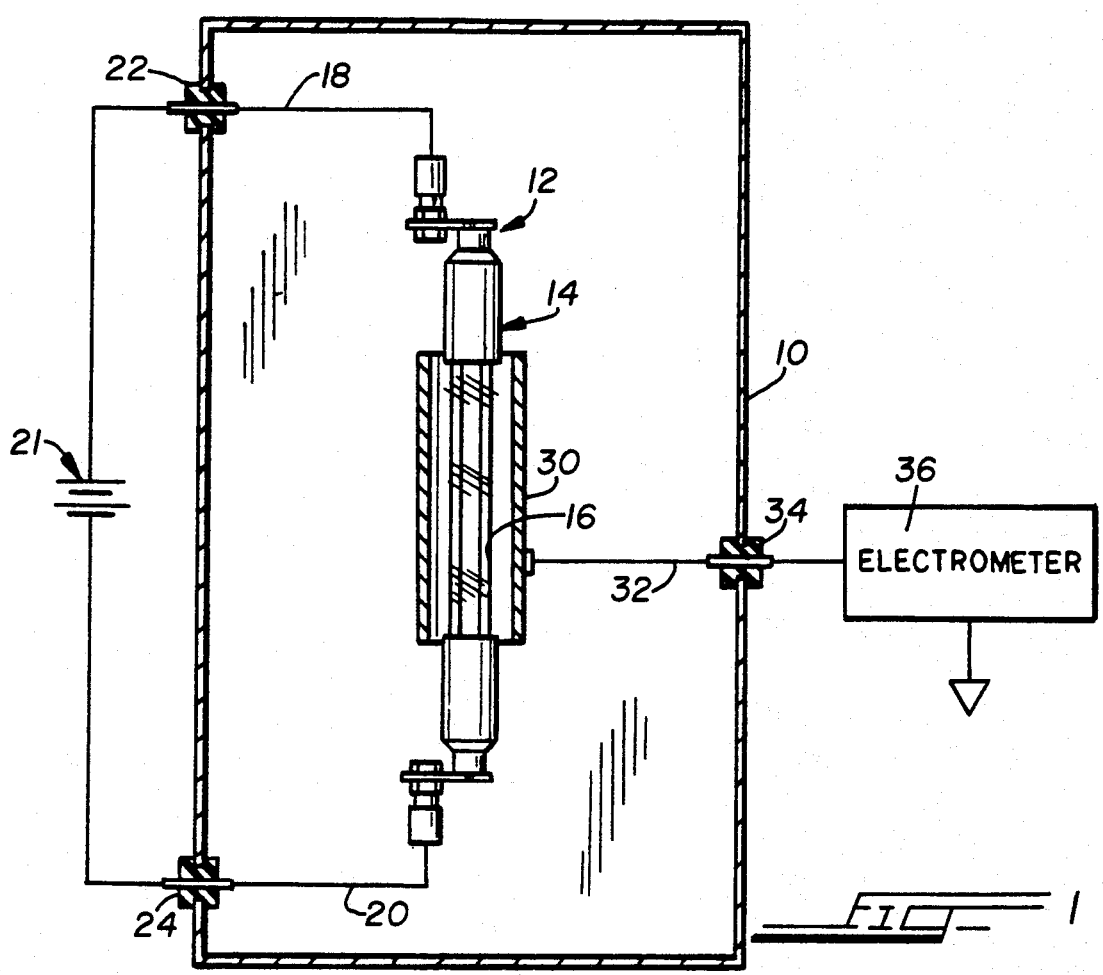
FIG. 1 is a cross-sectional view showing a vacuum-chamber in which the partial pressure of a gas is to be measured, which vacuum-chamber is shown with the partial-pressure gauge-apparatus of the invention therein.

Referring now to the drawings in greater detail, there is shown in FIG. 1 a conventional vacuum-chamber 10 which may be used in any kind of conventional, vacuum-processing techniques, for example sputtering and plasma etching. Water vapor in sufficient amounts will adversely affect these processes; thus, it is very important to detect and know what amounts of water vapor are present, as represented by the partial pressure thereof. This measurement of the partial pressure of water vapor in the chamber 10 is achieved by means of the partial-pressure gauge-apparatus 12 of the invention that is suspended in the vacuum-chamber 10. The partial-pressure gauge-apparatus 12 is made up of a light source, or lamp, 14 having an ultraviolet (UV) light bulb 16 that produces a combined UV radiation of 185 nanometers wavelength and 254 nanometers wavelength. The lamp 14 is a commercially available device manufactured by Danielson Associates, Inc., Lisle, Ill., under the name "PHOTOTRON", which is disclosed in U.S. Pat. No. 4,660,297, and which is used for desorbing water from the inner walls of a vacuum chamber. The lamp 14 is suspended within the vacuum chamber by means of conventional conductor-leads 18, 20, which serve the dual function of providing electrical connection to a power source 21 and supporting the lamp in the chamber. Since the conductor-leads are thin strips of steel, they may easily perform both functions, as is conventionally known in vacuum-processing technology. The leads 18 and 20 exit through the wall of the vacuum-chamber via conventional vacuum-flanges 22 and 24, respectively. The lamp 24 is constructed of vacuum-compatible materials and is designed to operate within a vacuum system without exploding. It also emits photons at the lower end of the UV spectrum where the photoelectric effect is greatest. Completely, and telescopingly, surrounding the bulb 16 is a cylindrical, or tubular, detector 30 made of nickel. Nickel is chosen as the detector material because it has a fairly low work function. Metals (sodium, cesium, potassium, etc.) with a lower work function (photoelectrons out for photon energy in) are less preferred because they may be too chemically active to allow constant exposure to air. Nickel also is a good vacuum material, since it is easy to work and to acquire in pure form. The cylindrical detector 30 is suspended, or supported, in the vacuum-chamber 10 by means of its own conductor-lead 32, in the same manner as described above for the leads of the lamp 14. The lead 32 exits the vacuum-chamber via a vacuum-flange 34, which lead is connected to a conventional electrometer 36 for detecting the current produced at the cylindrical detector 30, as described below in greater detail.

Figure 2:
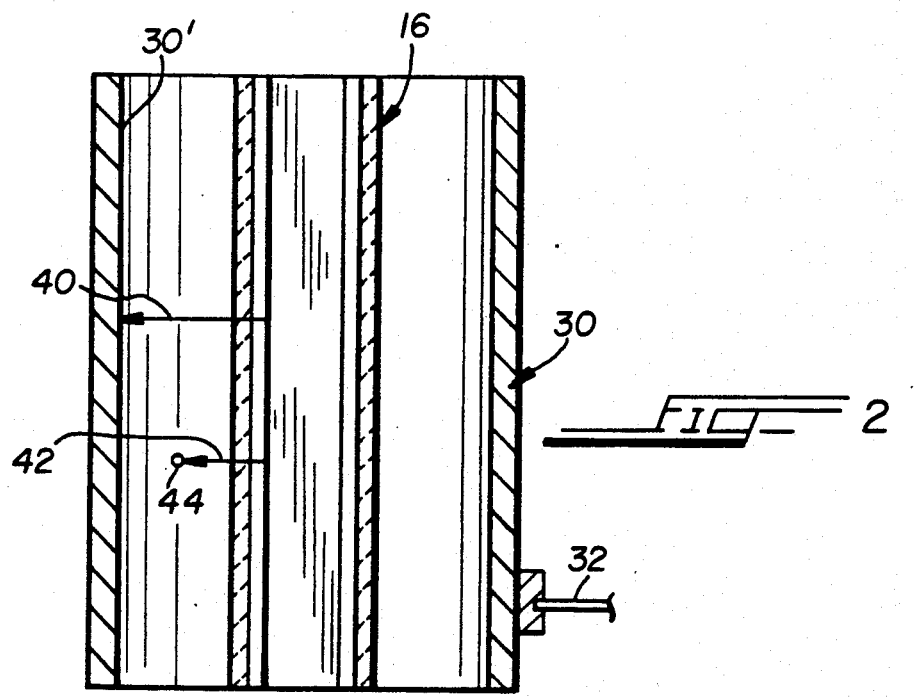
FIG. 2 is a detailed view, in cross section, showing the UV lamp-source of the invention telescopingly received through the nickel detecting cylinder of the partial-pressure gauge-apparatus of the invention.

FIG. 2 illustrates the concept by which the partial-pressure gauge of the invention works. Rays 40, 42 of ultraviolet light of the above-mentioned wavelength are excited by the UV light bulb source 16. If a water molecule 44 is present, it is struck by one or more light rays, which transfers energy to the water molecule by photonic absorbtion, as explained in U.S. Pat. No. 4,660,297, where such absorbtion-phenomenon is used for desorbing the water molecules from the wall of the vacuum-chamber so that they may be more readily pumped away, in order to achieve a more perfect vacuum in the vacuum-chamber. The greater the number of water molecules 44 in the annular space between the bulb 16 and the nickel detecting cylinder 30—or the more photonic energy absorbed by water molecules—the less amount of light reaching the inner surface of the 30' of the detecting cylinder 30. The converse is also true. When the UV radiation strikes the nickel material of the detecting cylinder, electrons are excited and electricity produced, in accordance with the well-known photoelectric effect. Thus, the greater the number of water molecules in the annular space, the fewer photoelectric excitation, and, therefore, a smaller current is produced, as measured by the electrometer 36. When fewer water molecules are present, the greater will be the photoelectric effect, and the greater the current that will be detected by the electrometer 36. It may, therefore, be seen that the partial pressure of the water vapor in the vacuum-chamber 10 is directly proportional to the number of water molecules present, and, therefore, is inversely proportional to the size of the current produced as measured by the electormeter 36.

Figure 3:
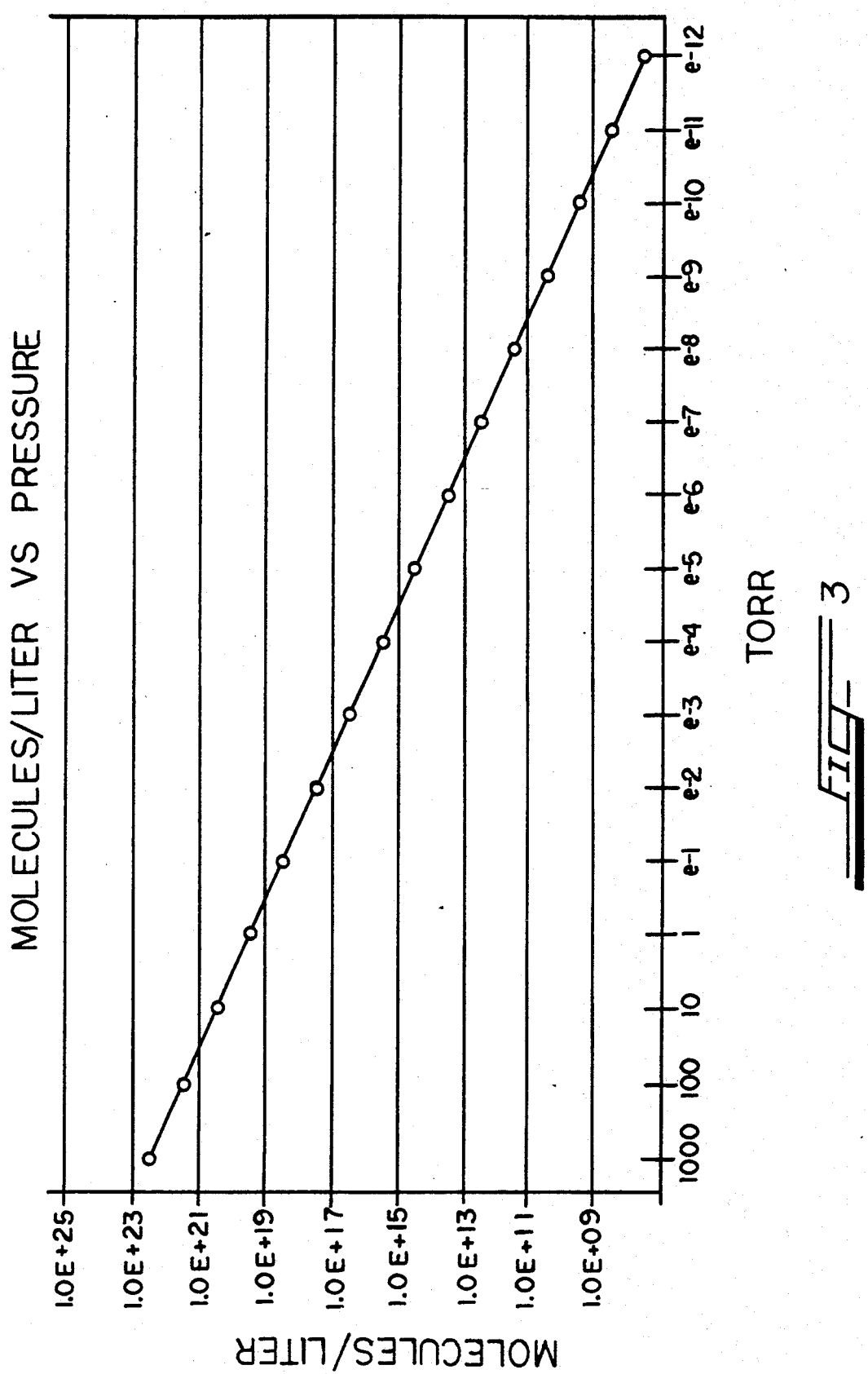
FIG. 3 is graph showing the number of molecules/liter between the UV lamp-source and the nickel detecting cylinder as determined by the total pressure within the vacuum-chamber.
Figure 4:
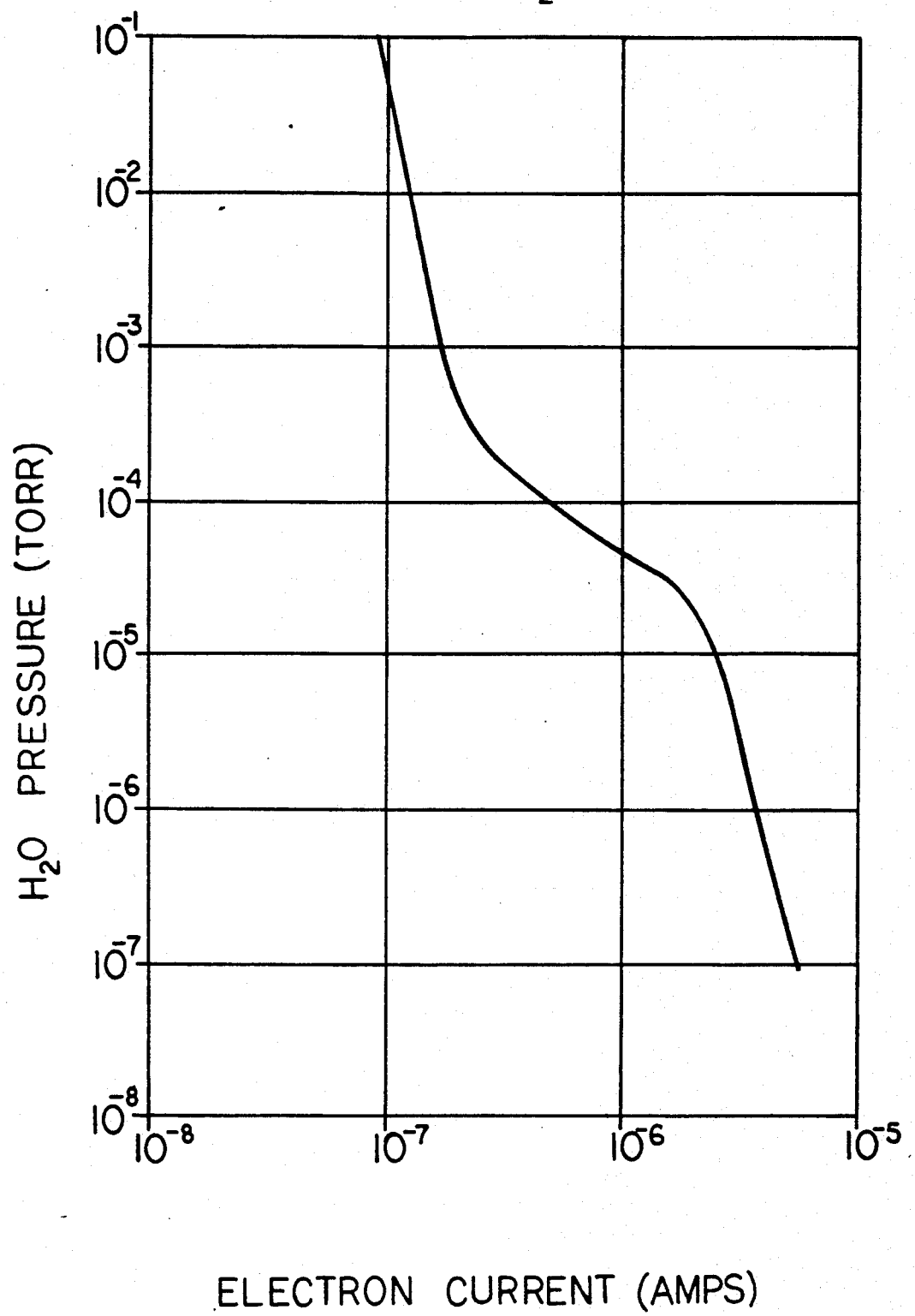
FIG. 4 is a graph showing the sensitivity of the partial-pressure gauge apparatus of the invention for measuring the partial pressure of water vapor between $10^{-1}$ torr and $10^{-7}$ torr.

FIG. 3 is a graph showing the direct proportionality of the amount of water molecules present and the partial pressure thereof. FIG. 4 is a graph showing the partial pressure of water vapor vs. the current detected by the electrometer 36, which curve shows the inverse proportionality of the partial pressure to the current. It should be noted that for initial tests carried out, the curve of FIG. 4, for pressures below $10^{-5}$, assumes a more linear shape, in contradistinction to the asymptotic shape for pressures above $10^{-5}$ The transition of the curve at about $10^{-5}$ torr to a more linear shape may be accounted for by the fact that in high vacuum pressure ranges ($10^{-5}$–$10^{-7}$ torr), the amount of water vapor liberated from the walls of the detecting cylinder 30 may become relatively and proportionally larger to the overall quantity of water molecules in the vacuum chamber space itself, which liberation of the water vapor in the walls of the detecting cylinder occur as the UV radiation excitates these water molecules, causing their desorbtion, as set forth in U.S. Pat. No. 4,660,297. However, whatever the graph may be, the gauge of the invention is calibrated to ensure that it operates and functions for all pressure ranges from atmospheric to ultrahigh vacuum, where pressures are as low $10^{-7}$ torr. It is, also, possible to use the gauge of the invention for vacuums where pressures may be $10^{-10}$ torr.

It is, also, noted that, not only does the gauge of the invention allow for the detection and measurement of the partial pressure of a gas in a vacuum, or even at atmospheric, but it does so while operating at room temperature, and utilizing a simple control and measurement circuit that will operate over the entire pressure range. Many prior-art, full-pressure, vacuum-gauges, such as ion gauges, require a filament that operates above 2,000 degrees C., which means that it will burn out frequently, and require replacement of the entire sensing tube. The heat generated requires a separate heating circuit to "degas" the elements of the sensing tube, and this, not only shortens the tube's lifetime, but requires an expensive gauge-control circuit. The hot filament is also prone to chemical reactions with process gases that also severely shorten lifetime.

While the gauge-apparatus 10 has been described above for use in detecting the partial pressure of water vapor from atmospheric to ultra-high vacuum, it may also be used for detecting and/or measuring the partial pressure of other gases, as well. For other gases, the electromagnetic radiation used, and its wavelength, would not necessarily be the same as that above-described for water vapor. As described above, for measuring the partial pressure of water vapor, the lamp 14 uses a bulb 16 that generates ultraviolet radiation having both 185 nanometers wavelength and 254 nanometers wavelength. This has been used for water vapor, since water vapor absorbs photonic energy for these wavelengths of UV radiation. For other gases, the electromagnetic radiation excited by the lamp 12, and its wavelength or range of wavelengths, will differ. For example, another gas whose partial pressure is extremely important to measure in a vacuum chamber is carbon monoxide (CO). CO has a negative influence on many vacuum-processes, and causes a loss of the level of control in the process, such as in crystal growth, where the presence of CO causes surface defects, haze and pits in the crystals. Another vacuum-process where carbon monoxide is detrimental is vacuum implant, where cross-contamination occurs if the carrier gas has CO contaminats. There are many other vacuum-processes where the presence of carbon monoxide above a certain level will adversely affect the results. Therefore, it is extremely important to detect and measure the presence of the carbon monoxide in the vacuum chamber, in order to reduce the quantity to acceptable, quality-control levels. According to the invention, for detecting and measuring the partial pressure of carbon monoxide in a vacuum chamber, the bulb 16 is chosen so that it produces ultraviolet radiation having a wavelength of 335 nanometers. A different, conventional bulb 16 that generates UV radiation in this wavelength is used. This wavelength of UV radiation will excite carbon monoxide molecules with photonic momenta-transfer, just as the other, above-listed wavelengths of UV radiation will excite water vapor molecules. A graph similar to that of FIG. 4 may be made for carbon monoxide gas. The same cylindrical detector 30 made of nickel would still be used for detecting the amount of UV radiation not experiencing photonic momenta-transfer, with the electrometer 36 indicating the amperage of the electricity generated by the photoelectric effect, in the same manner as above-described for the measurement of the partial pressure of water vapor. Thus, for the measurement of the partial pressure of carbon monoxide, the apparatus 12 would only differ from the case of water vapor by the type of conventional bulb 16 used.

Other gases, besides water vapor and carbon monoxide, may also be detected and/or measured for their partial pressures according to the method of the invention. For other gases, different electromagnetic radiation, such as infrared, X-ray, etc., may be required. However, the concept of the invention would be the same: To wit, the election of a specific electromagnetic radiation of a particular wavelength or range of wavelengths, which will excite the gas whose partial pressure is to be measured by the photonic energy of the respective electromagnetic radiation. While for ultraviolet radiation, as described above, the detector 30 relies upon the photoelectric effect to indirectly detect and measure the amount and partial pressure of water vapor or carbon monoxide, for different electromagnetic radiation, the means by which the unabsorbed light rays may be detected will vary, and be different from the photoelectric effect. For infrared electromagnetic radiation, IR photodiodes would be used; for X-rays, conventional X-ray detectors would be used.

As explained above, the gauge 10 may be used just to detect the particular gas, rather than going on to measure its partial pressure. This is done after the gauge has been calibrated, and may be used to detect the presence of a gas in a chamber at atmospheric or in a vacuum. This may be useful in a case, for example sputtering, where one may not wish to have any water vapor molecules at all in the vacuum chamber, because of the very expensive equipment.

While specific embodiments of the invention have been shown and described, it is to be understood that numerous changes and modifications may be made therein without departing from the scope, spirit and intent of the invention as set forth in the appended claims.

What I claim is:

1. A method of detecting a gas in a chamber, comprising:
   (a) generating electromagnetic radiation that will specifically be absorbed by the gas molecules to be detected in the chamber;
   (b) irradiating at least a portion of the interior of a chamber with the electromagnetic radiation of step (a);
   (c) said step (b) inherently causing gas molecules to be detected in the chamber to absorb energy by photonic energization;
   (d) said step (b) further comprising causing the electromagnetic radiation to emanate from a source at a first location in the chamber;
   (e) placing a detector of the electromagnetic radiation in the chamber at a second location; and
   (f) detecting the amount of the electromagnetic radiation from said step (d) that strikes the detector;
   said step (e) comprising placing the detector of the electromagnetic radiation around the source of electromagnetic radiation.

2. The method according to claim 1, wherein said step (a) comprises generating ultraviolet electromagnetic radiation; said step (e) comprises placing a detector made of a material that will detect the ultraviolet electromagnetic radiation.

3. The method according to claim 2, wherein said step (e) comprises placing a detector made of a material that will detect the ultraviolet electromagnetic radiation by the photoelectric effect; said step (f) comprising detecting the size of the current produced by the photoelectric effect.

4. The method according to claim 1, wherein said step (a) comprises generating ultraviolet electromagnetic radiation of at least one of 185 nanometers wavelength and 254 nanometers wavelength.

5. The method according to claim 4, wherein said gas to be detected is water vapor.

6. The method according to claim 1, wherein said step (a) comprises generating ultraviolet electromagnetic radiation of 335 nanometers wavelength.

7. The method according to claim 6, wherein said gas to be detected is carbon monoxide.

8. The method according to claim 1, wherein said step (f) comprises producing electric current in proportion to the amount of electromagnetic radiation irradiating the detector, and measuring the electric current thus produced, whereby an indicator of the partial pressure of the gas is obtained.

9. The method according to claim 1, wherein said step (d) comprises suspending the source of electromagnetic radiation in the chamber; said step (e) also comprising suspending the detector in the chamber.

10. The method according to claim 1, wherein said steps (a) through (f) are carried out in a vacuum chamber having a pressure in the range from between near atmospheric down to $10^{-10}$ torr.

11. A method of measuring the partial pressure of a gas in a chamber, comprising:
    (a) generating electromagnetic radiation that will specifically be absorbed by the gas molecules whose partial pressure is to be measured in the chamber;
    (b) irradiating at least a portion of the interior of a chamber with the electromagnetic radiation of step (a);
    (c) said step (b) inherently causing gas molecules whose partial pressure is to be measured in the chamber to absorb energy by photonic energization;
    (d) said step (b) further comprising causing the electromagnetic radiation to emanate from a source at a first location in the chamber;
    (e) placing a detector of the electromagnetic radiation in the chamber at a second location;
    (f) detecting and measuring the amount of the electromagnetic radiation from said step (d) that strikes the detector;
    said step (e) comprising placing the detector of the electromagnetic radiation around the source of electromagnetic radiation.

12. The method according to claim 11, wherein said step (a) comprises generating ultraviolet electromagnetic radiation; said step (e) comprises placing a detector made of a material that will detect the ultraviolet electromagnetic radiation.

13. The method according to claim 12, wherein said step (e) comprises placing a detector made of a material that will detect the ultraviolet electromagnetic radiation by the photoelectric effect; said step (f) comprising measuring the current produced by the photoelectric effect.

14. The method according to claim 11, wherein said step (a) comprises generating ultraviolet electromagnetic radiation of at least one of 185 nanometers wavelength and 254 nanometers wavelength.

15. The method according to claim 14, wherein said gas whose partial pressure is to be measured is water vapor.

16. The method according to claim 11, wherein said step (a) comprises generating ultraviolet electromagnetic radiation of 335 nanometers wavelength.

17. The method according to claim 16, wherein said gas whose partial pressure is to be measured is carbon monoxide.

18. The method according to claim 11, wherein said step (f) comprises producing electric current in proportion to the amount of electromagnetic radiation irradiating the detector, and measuring the electric current thus produced.

19. The method according to claim 11, wherein said step (d) comprises suspending the source of electromagnetic radiation in the chamber; said step (e) also comprising suspending the detector in the chamber.

20. The method according to claim 11, wherein said steps (a) through (f) are carried out in a vacuum chamber having a pressure in the range between from near atmospheric down to $10^{-10}$ torr.

21. In a chamber for containing gas, the improvement comprising a system for detecting the presence of a particular gas in said chamber;
    said system comprising a source of electromagnetic radiation for placement in a first location of said chamber;
    a detector means comprising at least one portion thereof for placement in a second location of said chamber for detecting the electromagnetic radiation from said source, said at least one portion of said detector means being spaced from said source of electromagnetic radiation;

said source directing its emanation of electromagnetic radiation toward said at least one portion of said detector means;

said source of electromagnetic radiation being telescopingly received through said portion of said detector means, said portion of said detector means being tubular in shape.

22. The apparatus according to claim 21, wherein said source generates ultraviolet electromagnetic radiation, and said at least one portion of said detector means comprising photoelectric-effect means for detecting said ultraviolet electromagnetic radiation by the photoelectric effect; said detector means further comprising measuring means for measuring the electricity produced in said at least one portion of said detector means by said photoelectric effect.

23. The apparatus according to claim 22, wherein said measuring means for measuring the electricity produced in said at least one portion of said detector means by said photoelectric effect is positioned exteriorly of said chamber, said detector means further comprising connecting means connecting said measuring means to said at least one portion of said detector means, said chamber having at least through-opening through which passes said connecting means to said measuring means.

24. The apparatus according to claim 22, further comprising power supply means for supplying power to said source, said power supply means comprising a power supply, and connecting means for connecting said power supply to said source; said chamber having at least one one through-opening through which passes said connecting means.

25. The apparatus according to claim 21, wherein said chamber is a vacuum chamber.

26. The apparatus according to claim 22, wherein said source of electromagnetic radiation generates ultraviolet electromagnetic radiation of at least one of 185 nanometers wavelength and 254 nanometers wavelength for absorption by water vapor.

27. The apparatus according to claim 22, wherein said source generates ultraviolet electromagnetic radiation of 335 nanometers wavelength for absorption by carbon monoxide.

28. The apparatus according to claim 22, wherein said at least one portion of said detector means is made of nickel.

* * * * *